(12) United States Patent
Chen (10) Patent No.: US 6,929,732 B2
(45) Date of Patent: Aug. 16, 2005

(54) ELECTROPHORESIS SEPARATOR (75) Inventor: Hui-Wan Chen, Taipei (TW)

(73) Assignee: Wealtec Enterprise Co., Ltd., Taipei (TW)

( * ) Notice: Subject to any disclaimer, the term of this patent is extended or adjusted under 35 U.S.C. 154(b) by 678 days.

(21) Appl. No.: 09/963,564

(22) Filed: Sep. 27, 2001

(65) Prior Publication Data
US 2003/0057095 A1 Mar. 27, 2003

(51) Int. Cl.$^7$ ............................................. G01N 27/453
(52) U.S. Cl. ....................... 204/606; 204/600; 204/616; 204/619
(58) Field of Search ................................ 204/606, 600, 204/616, 619

(56) References Cited
FOREIGN PATENT DOCUMENTS

WO       WO 98/52031       * 11/1998

* cited by examiner

Primary Examiner—Ling-Sui Choi
(74) Attorney, Agent, or Firm—Bacon & Thomas, PLLC (57) ABSTRACT

An electrophoresis separator of which a receiving tank used for placing therein carriers has slots on the two sides thereof, one side of each carrier has a notch matching with a corresponding slot; so that when the carrier is inserted in the receiving tank, a blocking piece provided at the bottom of the receiving tank covers the bottom of the carrier and the crevice between the notch and the receiving tank; and a blocking sheet is inserted into the slot and notch. The blocking sheet can be removed from the slot and notch after the gel in the carrier is fixed and shaped, then the gel can contact the electric conducting liquid in the electrophoresis tank through the slot and notch; the other end of the gel body will contact the electric conducting liquid through an upper opening of the carrier directly. When electrodes are activated, electric current floating is resulted to cause an effect of molecule separation and analysis for the sample in the gel.

8 Claims, 14 Drawing Sheets

ELECTROPHORESIS SEPARATOR

BACKGROUND OF THE INVENTION

1. Field of the Invention

The invention is related to an electrophoresis separator, and especially to such an electrophoresis separator by which production of a sample is more convenient and the sample can be connected to the whole device more easily, thereby the whole electrophoresis separating engineering can be carried out more smoothly and surely.

2. Description of the Prior Art

Figure 1:
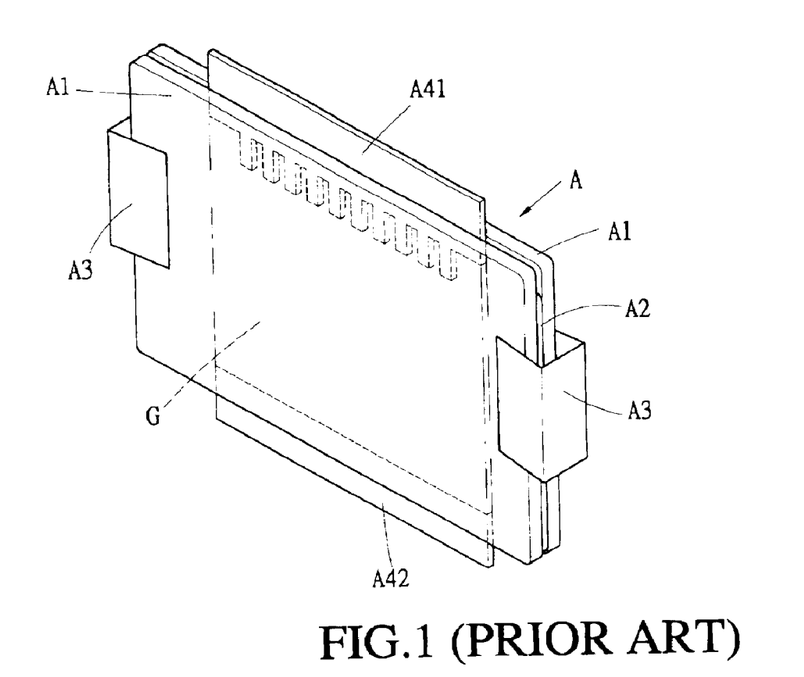
FIG. 1 is a schematic perspective view showing the structure of a sample carrier in a general gel electrophoresis method.
Figure 2:
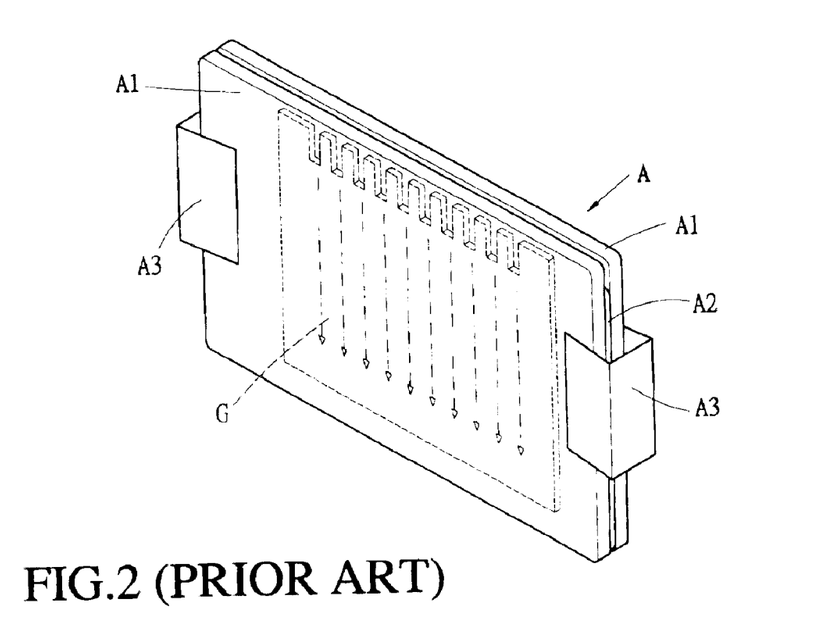
FIG. 2 is a schematic perspective view showing the way of generation of a molecule spectrogram in a general gel electrophoresis method.

An electrophoresis method in biologic technology mainly aims at separating and analysis of DNA, RNA and protein. Macromolecules of DNA, RNA and protein are separated according to the ratio of electric charge to mass, and the molecules are driven by means of electric current to make the molecules float on the gel of the substance. While in moving, the molecules will be separated because of the differences of the electric charges carried by the ion-natured ingredient and of the sizes of these molecules themselves. The sample solution to be separated and analyzed is dropped in the crevice of two clamping carriers. As shown in FIG. 1, a conventional carrier (A) for receiving sample solution is made from two glass sheets (A1) with a packing piece (A2) of proper thickness and a pair of clamps (A3) to clamp them firm. Then the crevice between the two glass-sheets (A1) are injected with gel (G) containing tracing dyestuff and sealed. A comb-like board A41 and a blocking member (A42) are provided in the upper and bottom openings respectively of the carrier (A) for fixing the shape of the gel. The electrophoresis separating engineering can be executed after the gel (G) is fixed and shaped, as shown in FIG. 2. Electric current is added to the gel (G), and stopped when stripes of the tracing dyestuff are moved over the length of the gel slice (G). A so-called molecule spectrogram will be formed at this time because of combination of the dyestuff with the protein or RNA on the gel in favor of observing and recording distribution of the sizes of the molecules in the sample solution.

Since characteristics of samples and the sizes of molecules are different, thickness of the gel slices used in the electrophoresis separating method will be different. There are three kinds of thickness 0.75 mm, 1.0 mm and 1.5 mm in general, and the thickness is determined by the packing piece (A2) between the two glass-sheets (A1) of the carrier (A); thereby, when in using the conventional carrier (A) to fix the sample solution, the glass sheets (A1) shall be dismantled frequently in order to change a packing piece slice (A2) of a different thickness for use. The breakage phenomenon of the glass sheets (A1) happens easily during the dismantling procedure and makes them unable to use again. The clamps (A3) only have the clamping function and are unable to position these two glass-sheets (A1) effectively. The effect of production of the sample will be affected by moving of these two glass-sheets (A1) during the procedure of injecting and sealing the gel. Especially after completing injecting and sealing of the gel, the whole carrier (A) needs to be put on a receiving shelf to fix the carrier (A) for waiting for being fixed and shaped of the gel. Thereby, the whole production procedure of the sample becomes complicated and is subjected to causing damage of the device and the sample.

Figure 3:
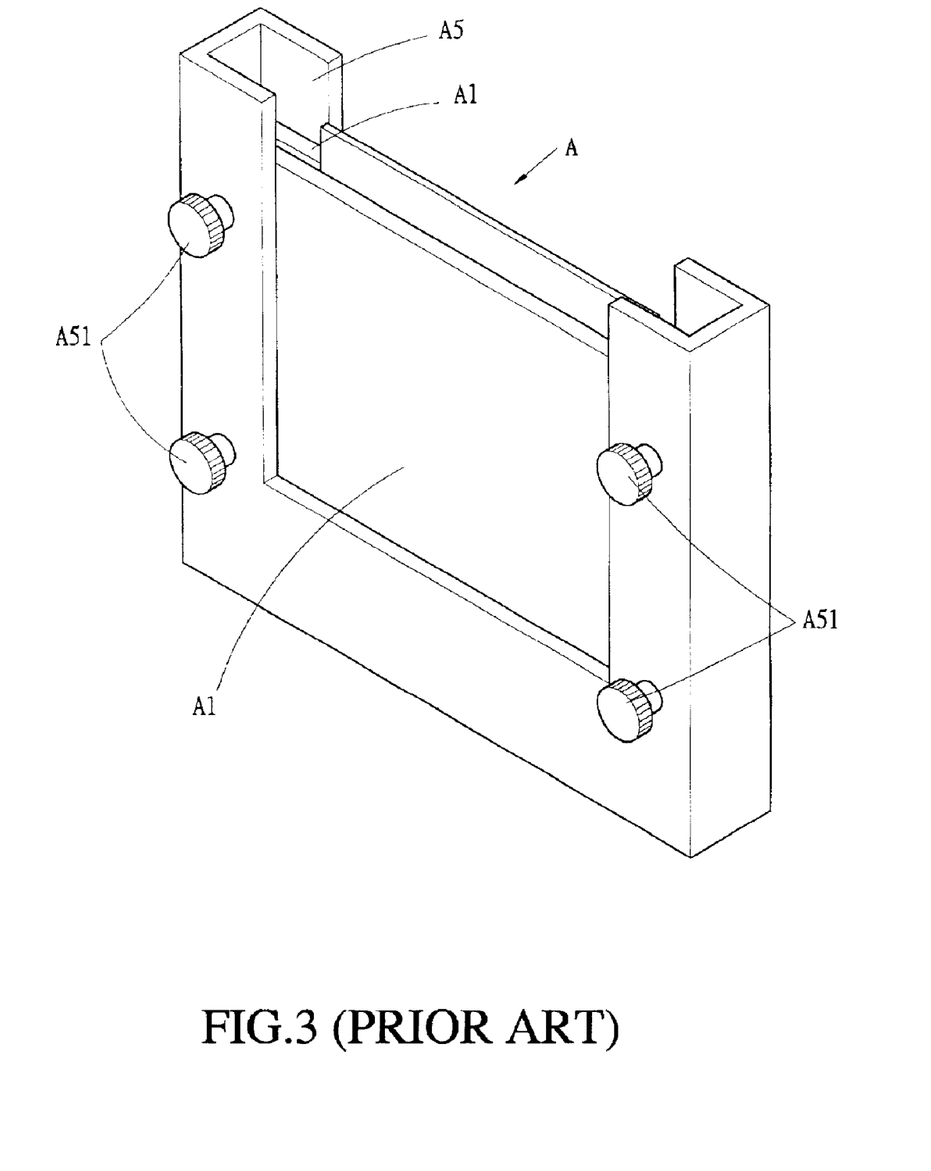
FIG. 3 is a schematic perspective view showing the structure of another conventional sample carrier.

As shown in FIG. 3, in order to eliminate the known defects resided in the abovementioned utilization of carrier and clamps, a structure of frame (A5) is used directly to adjust the crevice of these two glass-sheets (A1). By adjusting the depth of screwing of a screw (A51), a result of adjusting the crevice between these two glass-sheets (A1) will be obtained directly. However, there are more than four points to be fixed for every set of glass sheets (A1), it is impossible to adjust the depth of every screw (A51) in a fast and accurate way. Thus the crevice between the glass sheets (A1) will be uneven, and especially the glass sheets (A1) will be damaged because of over rotating of the screw (A51). And after completing the action of injecting and sealing the gel, the whole carrier still needs to be put on a receiving shelf for waiting for being fixed and shaped of the gel. Besides, the conventional electrophoresis separator mainly uses an electrophoresis tank to do separation and analysis of the molecules, while the abovementioned two structures of the carrier still need to be moved into the electrophoresis tank after production of the sample of the carrier is completed. Then the carrier is positioned through a complicated fixing action, so it is still not as convenient in use as expected.

SUMMARY OF THE INVENTION

Accordingly, the electrophoresis separator of the present invention includes an electrophoresis tank and a receiving tank as the main body of the entire electrophoresis separator, and electrodes for driving electric current are provided and electric conducting liquid as an electric current passage is formed separately in the electrophoresis tank and receiving tank. Wherein, the receiving tank is a case which can be installed directly in the electrophoresis tank, and is mainly used for placing therein carriers and is provided with two slots respectively on the two sides thereof to communicate with the electrophoresis tank. One side of the carrier is provided with a notch matching with its corresponding slot. When the sample solution is dropped on the carrier, the latter can directly be inserted in the receiving tank. A blocking piece provided at the bottom of the receiving tank covers the bottoms of the carriers and the crevices between the notches and the receiving tank, and blocking sheets are inserted into the slots and notches at the same time. The blocking sheets can be removed from the slots and notches after the gel filled in the carrier is fixed and shaped. Then the gel can contact the electric conducting liquid in the electrophoresis tank through the slots and notches; the other ends of the gel slice will contact the electric conducting liquid in the receiving tank through the upper openings of the carriers directly. When the electrodes in the electrophoresis tank and the receiving tank are in functioning, the electrons produced in the receiving tank by the electrodes can flow to the electrodes of the electrophoresis tank through the gel in the carriers. Thus electric current floating is resulted to cause an effect of molecule separation and analysis for the samples in the gel. And this is the prime object of the present invention.

Another object of the electrophoresis separator of the present invention is to connect two clamping sheets to form a structure of which positioning is sure for receiving a carrier which receives sample solution therein. In which, positioning pins and positioning holes are provided on the two clamping sheets respectively. There are protruding sockets all of a specific height provided on one of the two clamping sheets on the surface to be contacted with the other clamping sheet. When the two clamping sheets are abutted upon each other, the protruding sockets can form a crevice between the two. This will enable an operator to position the clamping sheets of the carrier promptly and get a thickness of the gel accurately after shaping.

The third object of the electrophoresis separator of the present invention is to provide clamping members on the clamping sheets of each carrier directly. When the two clamping sheets are abutted upon and positioned relative to each other; the clamping members can be directly used to fix and clamp them.

A further object of the electrophoresis separator of the present invention is to provide elastic sheets sandwiched between the two clamping sheets of each carrier in order to increase compactness between the two clamping sheets and help shaping of the gel so as to avoid gel spilling.

The present invention will be apparent after reading the detailed description of the preferred embodiment thereof in reference to the accompanying drawings.

DETAILED DESCRIPTION OF THE PREFERRED EMBODIMENT

Figure 4:
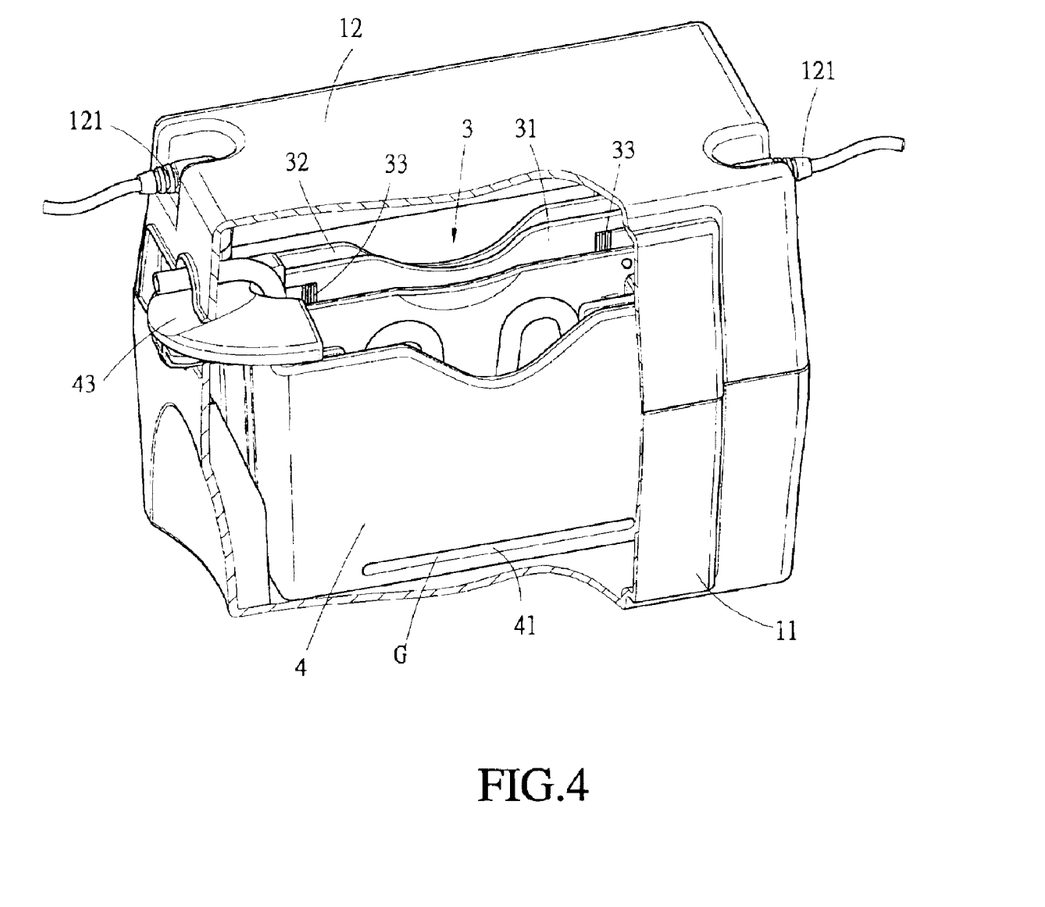
FIG. 4 is a schematic perspective view showing the whole structure of the device of the electrophoresis separator of the present invention.
Figure 5:
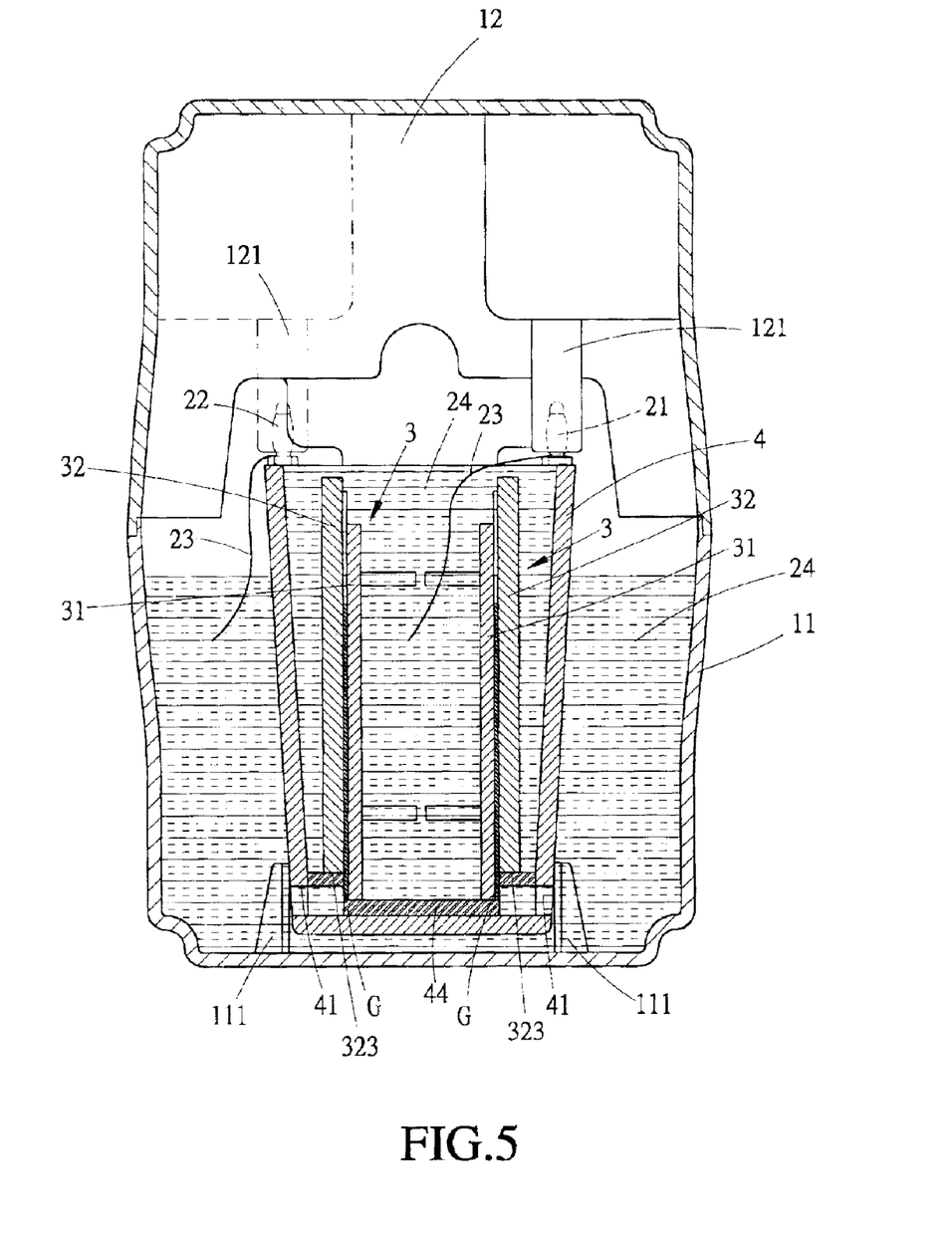
FIG. 5 is a sectional view showing the structure of the whole device of the electrophoresis separator of the present invention.

The electrophoresis separator of the present invention is shown in FIG. 4 and FIG. 5, the structure of the whole device is comprised of an electrophoresis tank 11 and a receiving tank 4 as the main body. The electrodes for driving the electric current are provided in the electrophoresis tank 11 and the receiving tank 4 separately. A cathode 21 and an anode 22 are provided simultaneously on the top of the receiving tank 4 in the structure of the embodiment shown. And the electrophoresis tank 11 and the receiving tank 4 are filled with electric conducting liquid 24 to form an electric current passage. Besides, the anode 21 and the cathode 22 are connected to the electric conducting liquid 24 in the electrophoresis tank 11 and the receiving tank 4 via conductors 23. Carriers 3 each for receiving a sample are immersed in the electric conducting liquid 24 of the receiving tank 4, and an upper lid 12 is used to cover the entire reaction device. An electrode connector 121 is provided on the upper lid 12 in favor of supplying the electric current for the electrodes.

Figure 7:
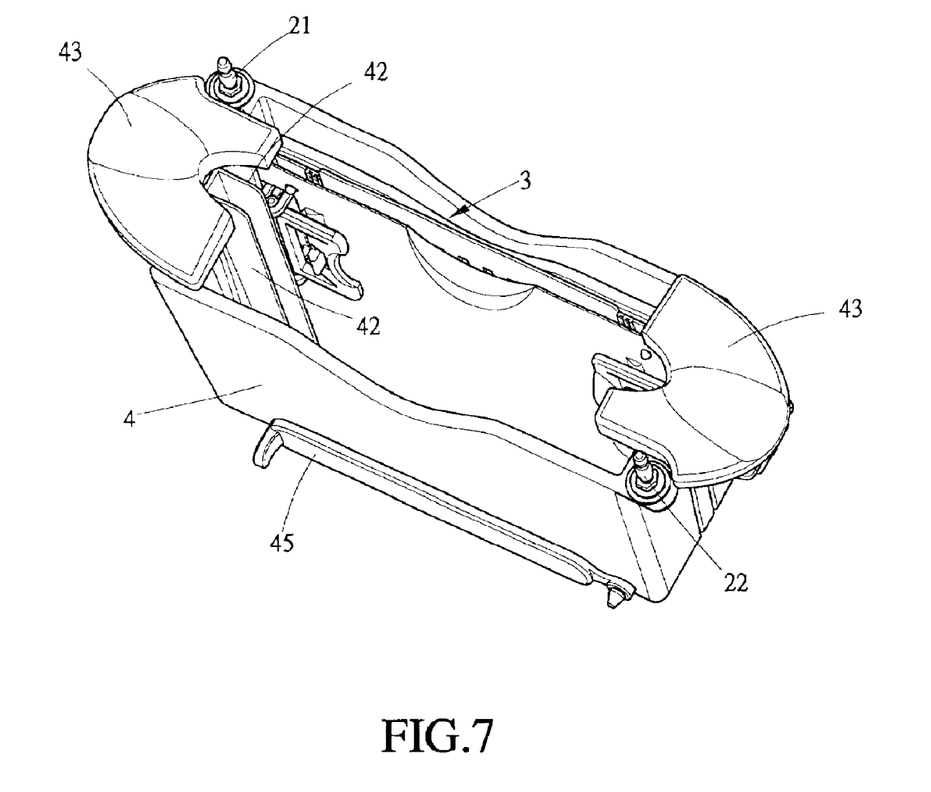
FIG. 7 is a schematic perspective view showing the assembled status of a carrier with the receiving tank of the present invention.
Figure 8:
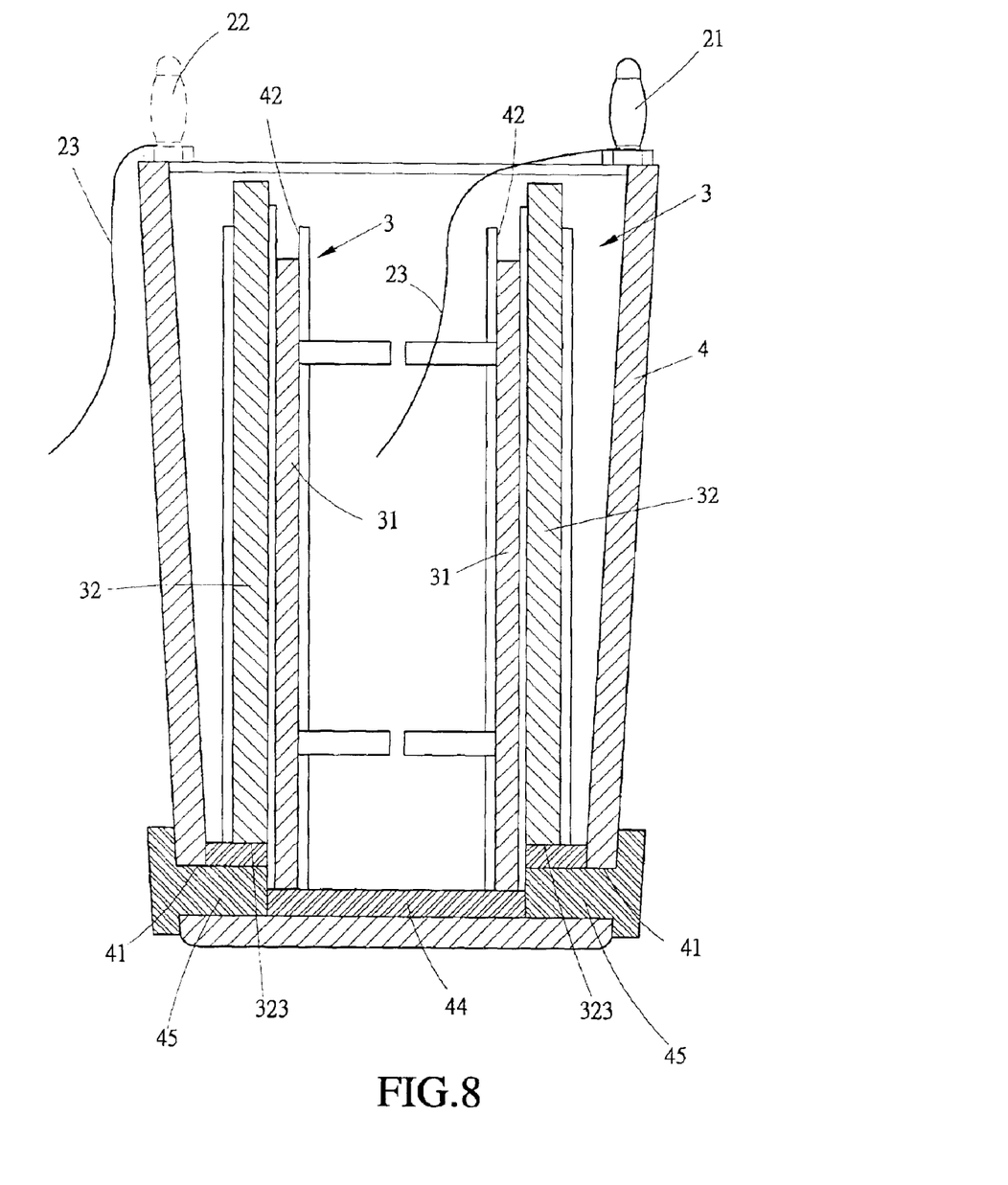
FIG. 8 is a sectional view showing the assembled status of the carrier with the receiving tank of the present invention.
Figure 9:
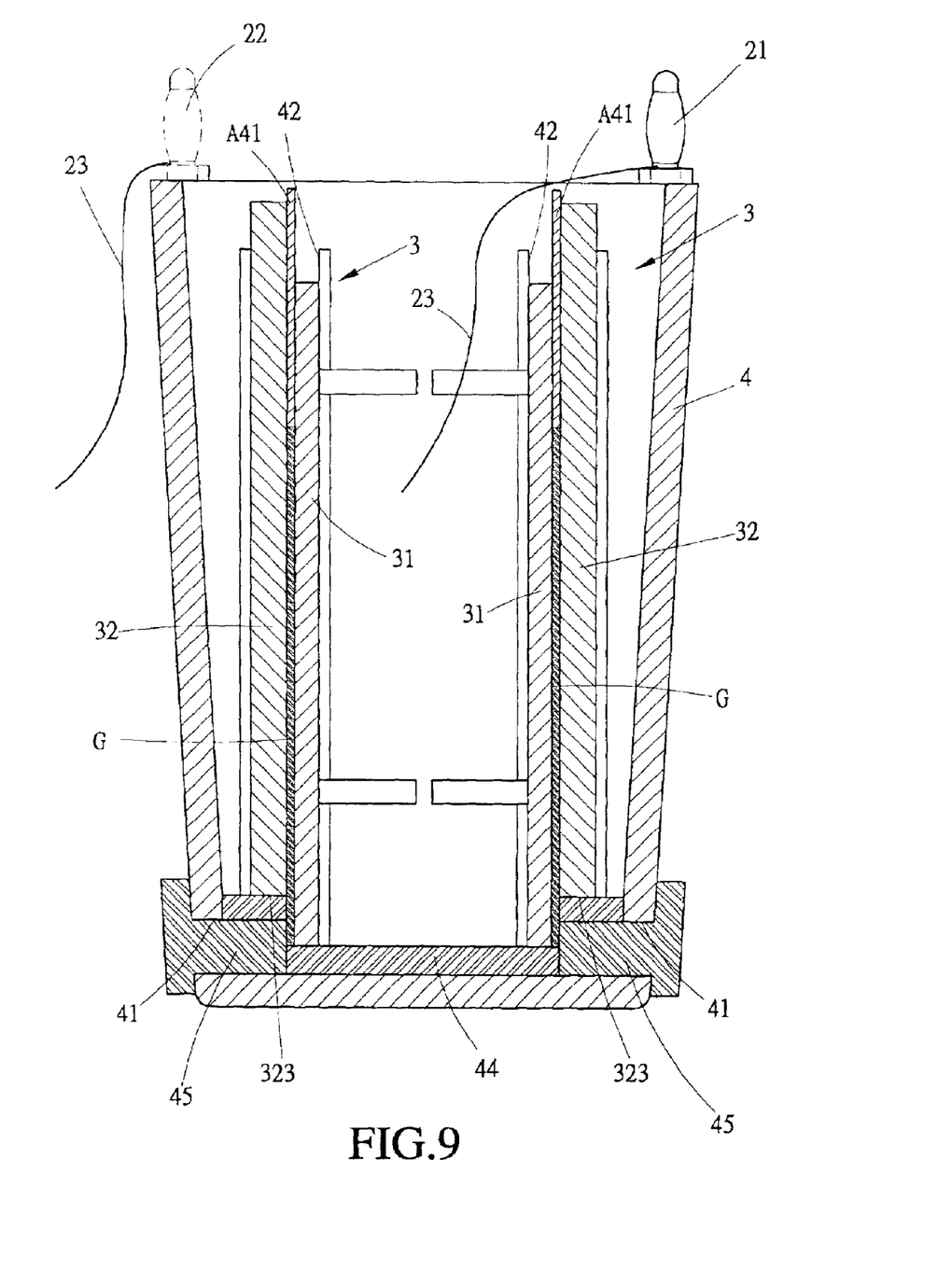
FIG. 9 is a sectional view showing the status of gel injecting and sealing in the present invention.

With regard to the receiving tank 4, it is a case and can be installed directly in the electrophoresis tank 11. The bottom of the electrophoresis tank 11 is provided with two positioning members 111 to matchably fix the receiving tank 4. A slot 41 in communicating with the electrophoresis tank 11 is formed on each side of the receiving tank 4. Each carrier 3 is made from two clamping sheets. The clamping sheets are divided into a first clamping sheet 31 and a second clamping sheet 32 according to their respective contours. The bottom of the first clamping sheet 31 forms a notch 323 correspondingly to one of the slots 41. As shown in FIG. 7 and FIG. 8, there are positioning grooves 42 provided in the receiving tank 4 to position the carriers 3, and press fixers 43 are provided on the top of the receiving tank 4 to fix the carriers 3. After the sample solution is dropped on the carriers 3, the latter can be inserted in the receiving tank 4. A bottom blocking piece 44 provided at the bottom of the receiving tank 4 will directly cover the bottom of the carriers 3 and the crevices between the notches 323 and the receiving tank 4. And blocking sheets 45 are inserted into the slots and notches at the same time. Then as shown in FIG. 9, the gel (G) is injected and sealed between first clamping sheets 31 and second clamping sheets 32 of the carriers 3 and a comb-like board A41 is provided on the upper opening of each carrier 3 to help shaping of the gel (G).

Figure 6:
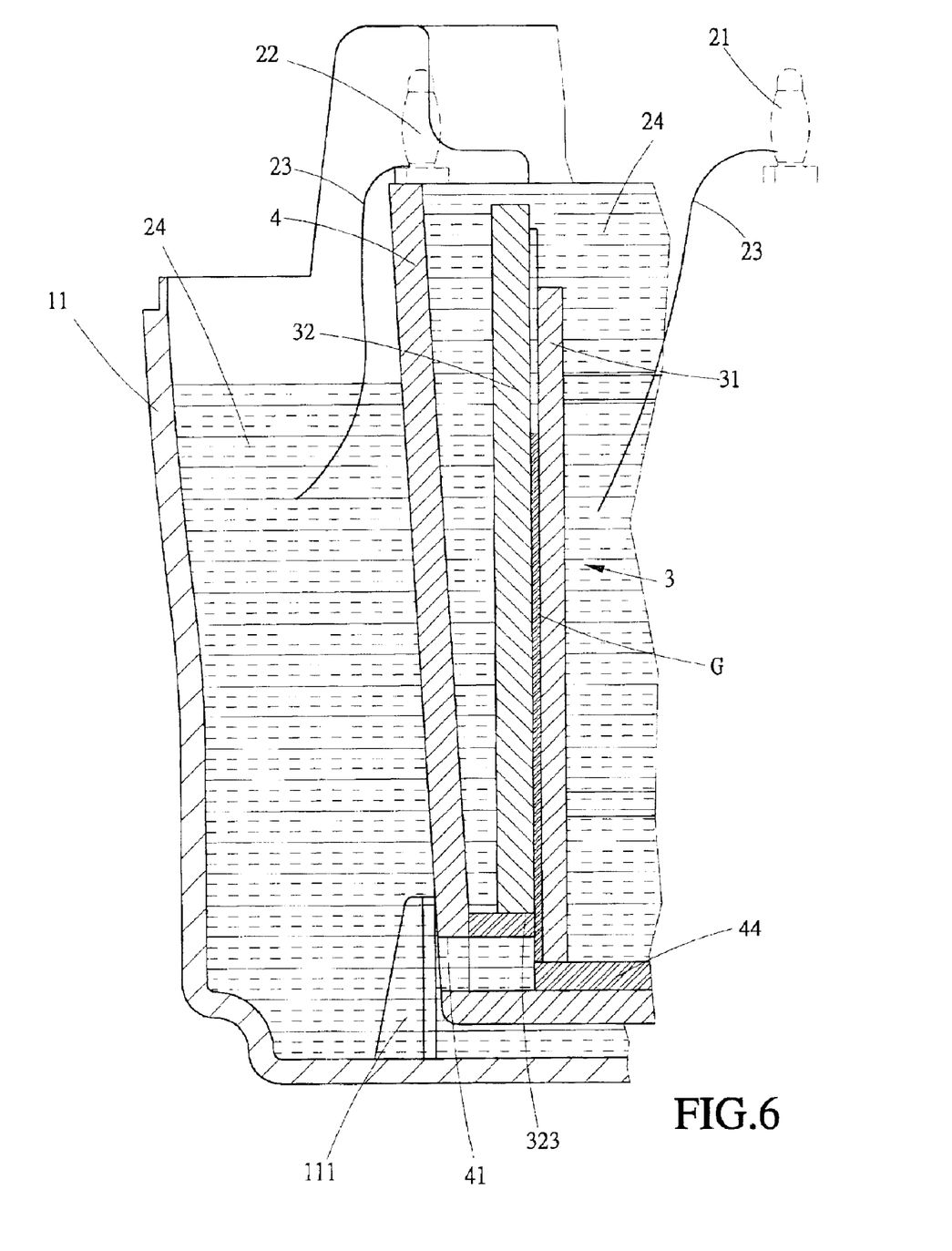
FIG. 6 is an exploded schematic sectional view showing the status of floating of the electric current in the present invention.
Figure 10:
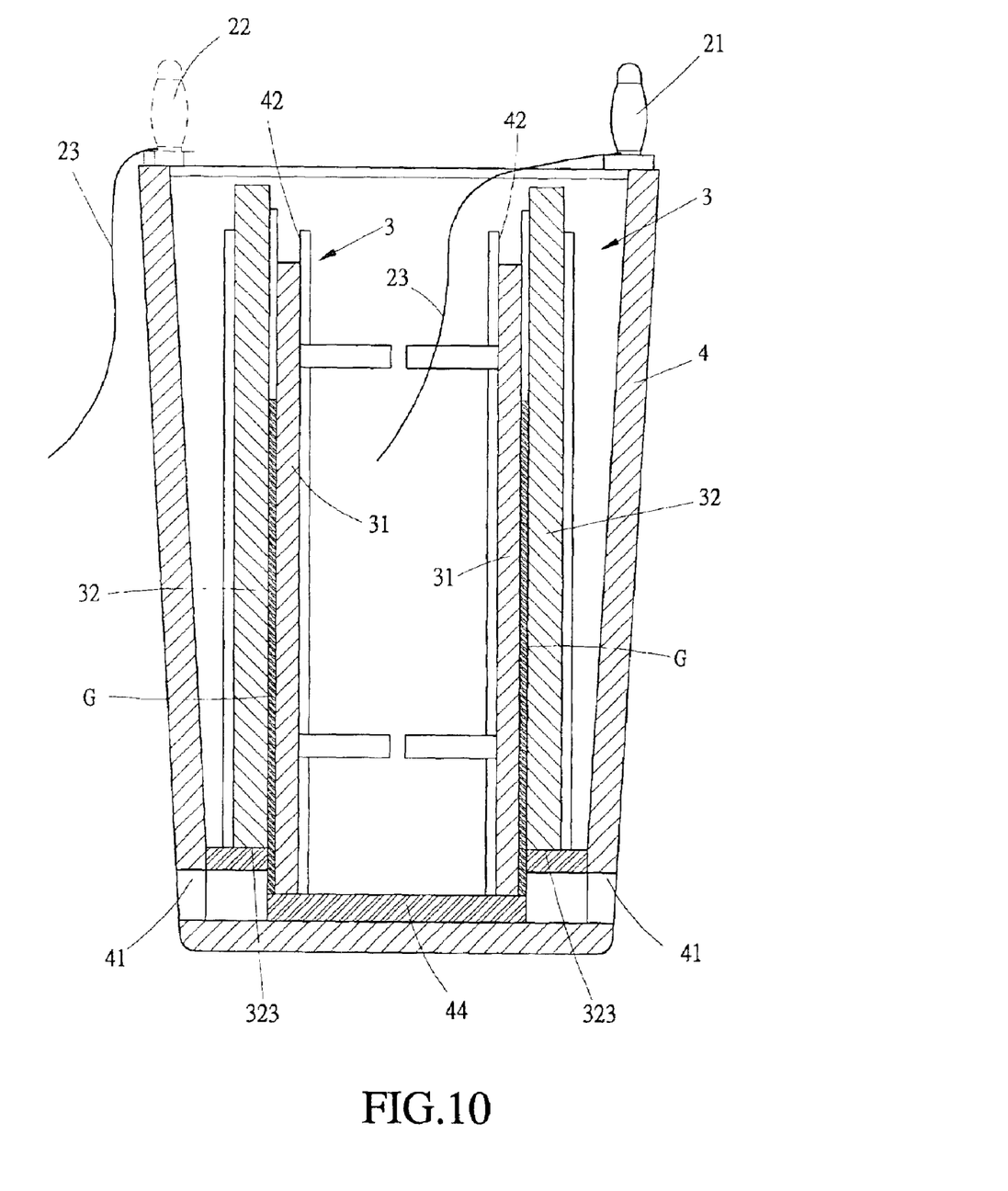
FIG. 10 is a sectional view showing the status of fixing and the shaping of the gel in the present invention.

After the gel (G) filled in the carriers 3 is fixed and shaped, the blocking sheets 45 at the slots 41 and the comb-like boards A41 can be removed to become the status shown in FIG. 10. Again as shown in FIG. 5 and FIG. 6, the whole receiving tank 4 is placed in the electrophoresis tank 11, and the electric conducting liquid 24 is added to the receiving tank 4 in order to make the gel slices (G) contact the electric conducting liquid 24 in the electrophoresis tank through the slots 41. The other ends of the gel slices (G) directly contact the electric conducting liquid 24 in the receiving tank 4 through the upper openings of the carriers 3. And positioning members 111 at the bottom of the electrophoresis tank 11 can be installed correspondingly beneath the slots 41 at the bottom of the receiving tank 4 to function as a reminder for the operator to remove the blocking sheets. While the electrodes are activated in the electrophoresis tank 11 and the receiving tank 4, electrons produced by an anode 21 in the receiving tank 4 can be drifted to a cathode 22 in the electrophoresis tank 11 through the gel (C) of the carrier 3. Thus a result of electric current floating is formed and this will cause an effect of molecule separation and analysis of the sample in the gel (G).

Figure 11:
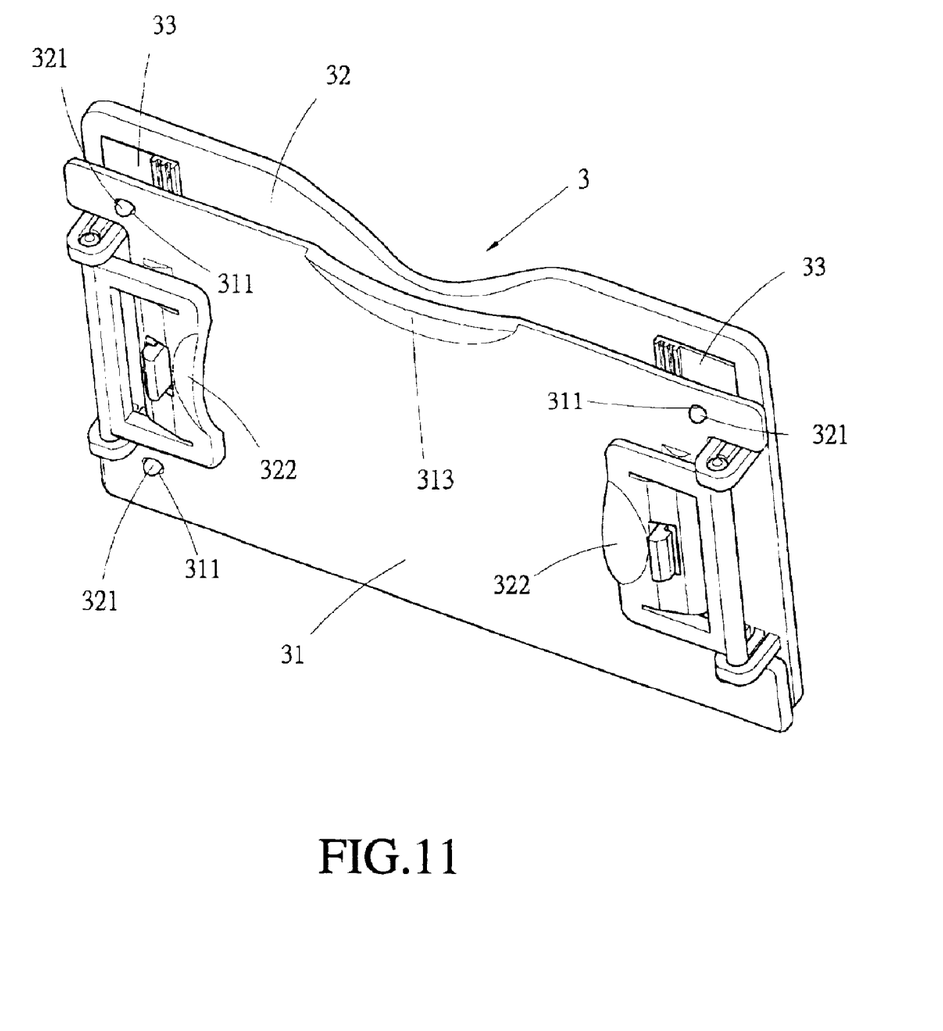
FIG. 11 is a perspective view showing the appearance of the structure of a carrier of the present invention.
Figure 12:
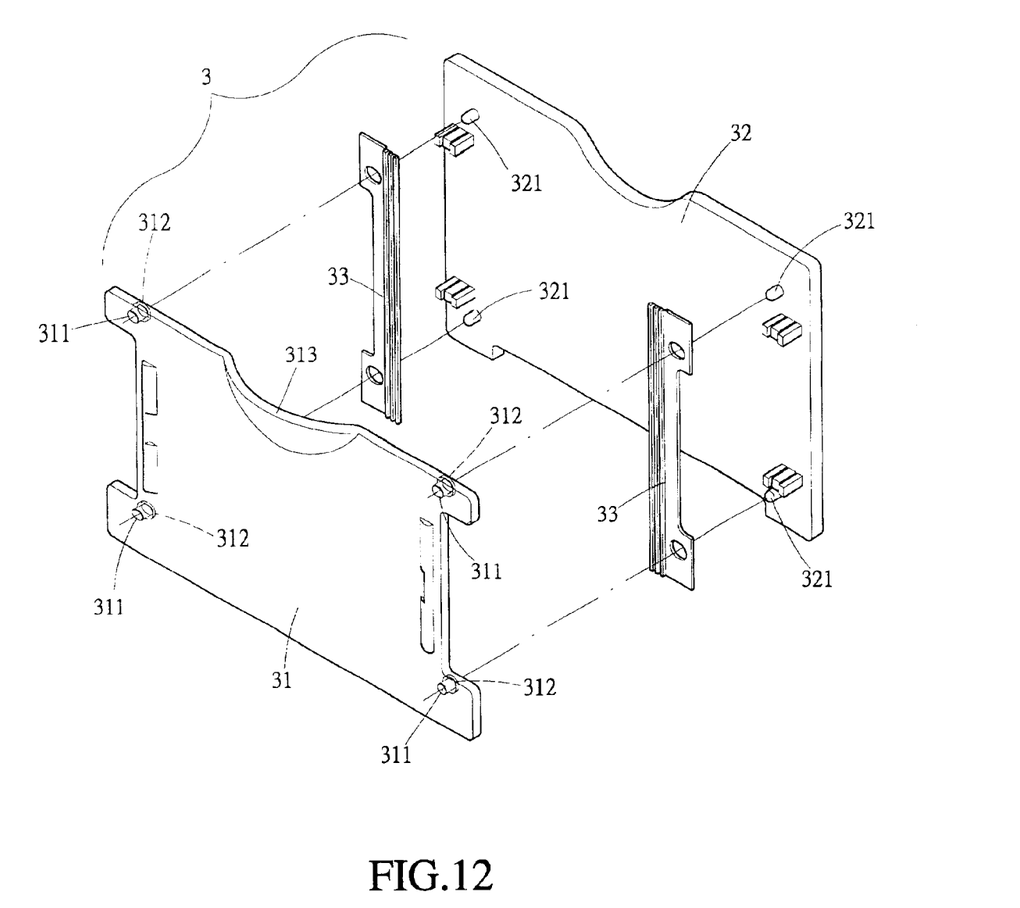
FIG. 12 is an analytic perspective view showing the structure of the carrier of the present invention.

Referring to FIG. 11 and FIG. 12 at the same time, the carriers 3 of the present invention are formed each by sure positioning of the first clamping sheet 31 and the second clamping sheet 32 to form a structure to receive the sample solution. There are positioning holes 311 and positioning pins 321 provided on the first and second clamping sheets 31, 32 respectively. There are protruding sockets 312 all of a specific height provided on each of the first clamping sheets 31 on the surface to be contacted with one of the second clamping sheets 32. When the two clamping sheets are abutted upon each other, the protruding sockets 312 can form a crevice between the two. This will enable an operator to position the first clamping sheet and the second clamping sheet 31, 32 of each carrier 3 promptly and get a thickness of the gel accurately after shaping by means of the positioning holes 311 and positioning pins 321. Besides, there are clamping members 322 formed on the second clamping sheet 32 of the carrier 3 directly, so that when the first and second clamping sheets 31, 32 are abutted upon and positioned relative to each other; the clamping members 322 can be directly used to fixedly clamp the first and second clamping sheets 31, 32 to assure firmness of the structure. Furthermore, an elastic sheet 33 can be sandwiched between each pair of the first and second clamping sheets 31, 32 of the carriers 3 in order to increase compactness between the two clamping sheets and help shaping of the gel so as to avoid gel spilling.

Figure 13:
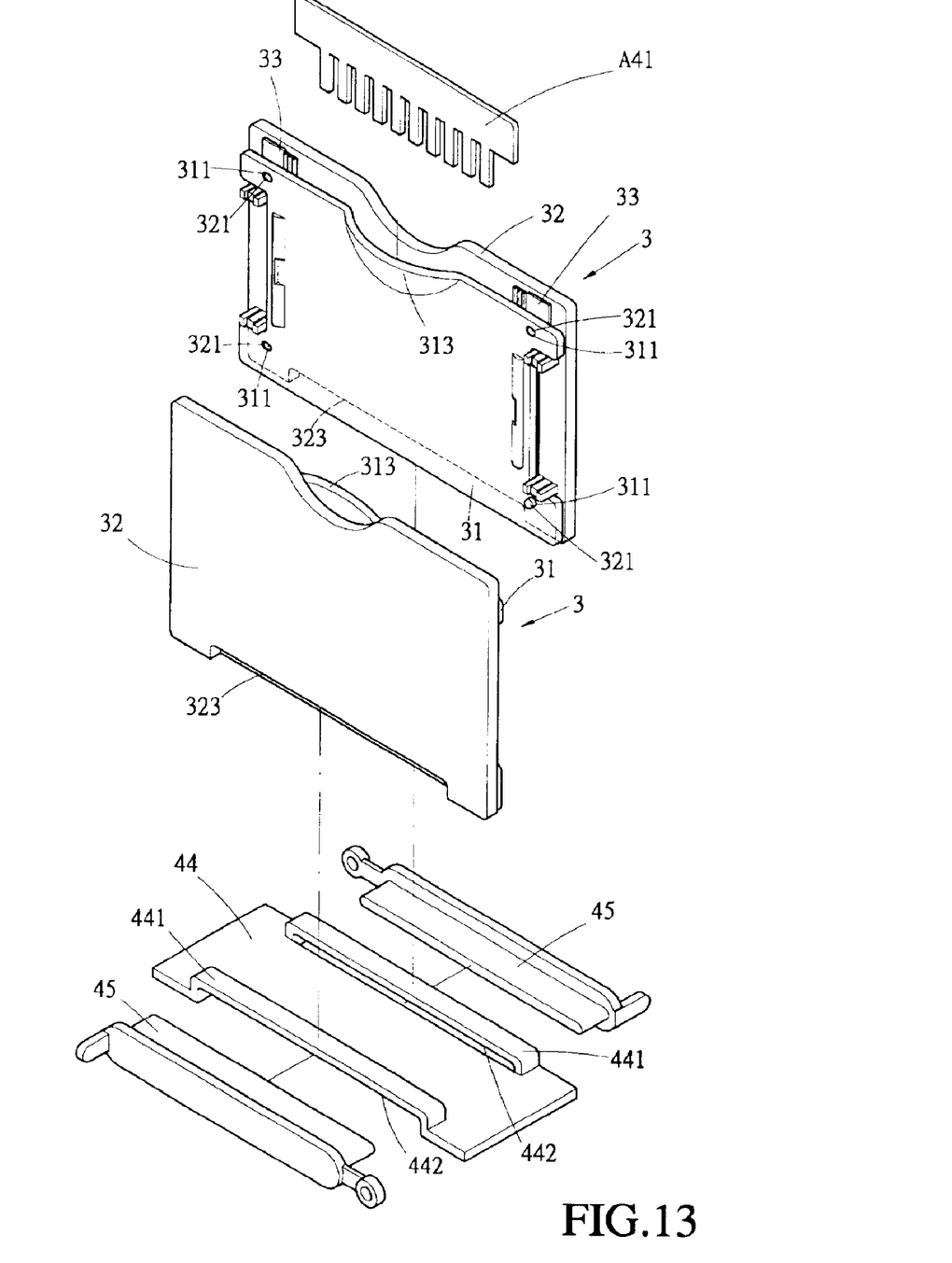
FIG. 13 is a schematic perspective view showing the related connecting positions of blocking sheets in the carrier and the receiving tank of the present invention.
Figure 14:
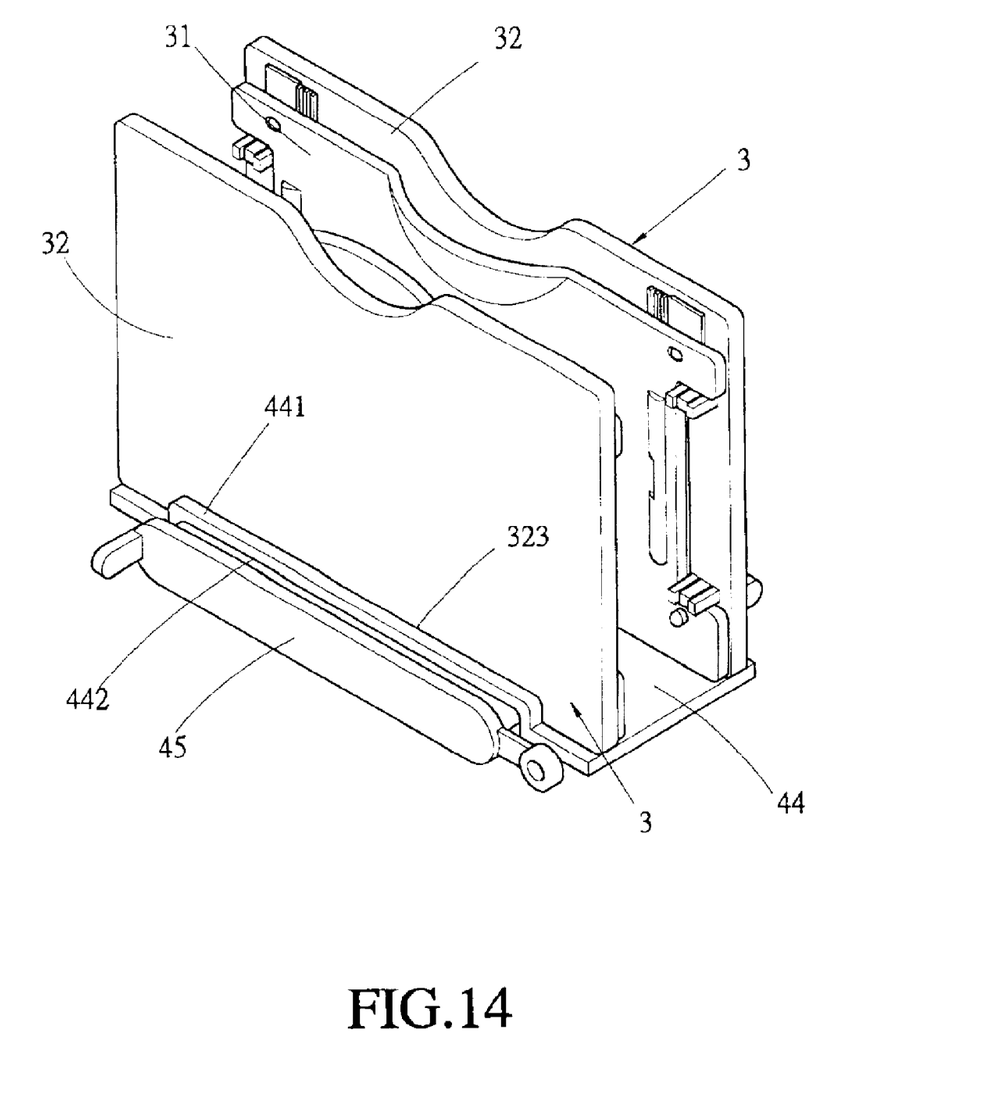
FIG. 14 is a schematic perspective view showing the status of connecting of the blocking sheets in the carrier and the receiving tank of the present invention.
Figure 15:
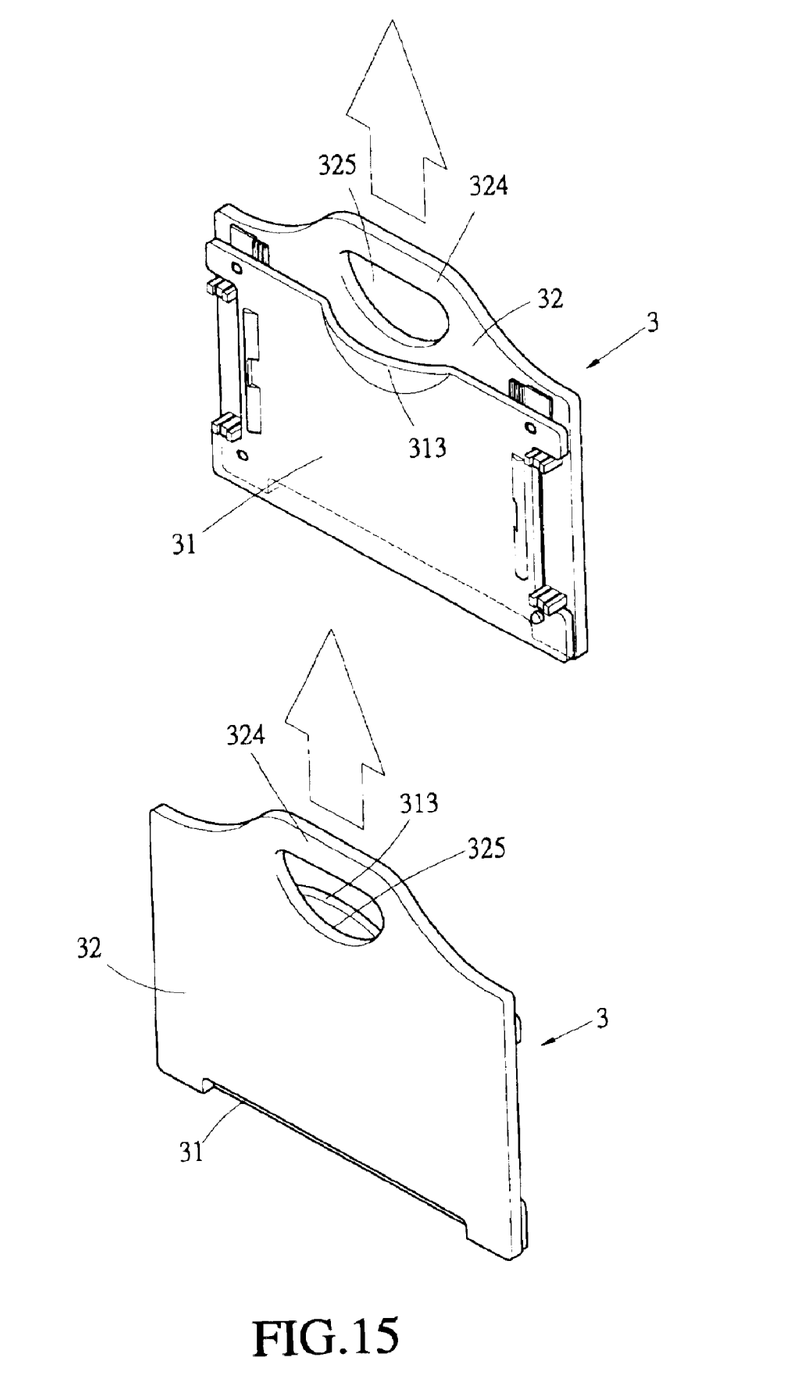
FIG. 15 is a perspective view showing the appearance of the structure of the carrier of another embodiment of the present invention.

As shown in FIG. 13 and FIG. 14, the first and second clamping sheets 31, 32 of the carriers 3 are ejection shaped of plastic material, they have the advantage of not being fragile; this will make it more convenient to design the contour of the clamping sheets. As shown in the figures, a notch 323 formed at the lateral of each carrier 3 can be provided at the bottom of a first clamping sheet 31 directly. And two fitting-in portions 441 are provided on the bottom blocking piece 44 to match and fit in the notches 323. An opening 442 is provided at each fitting-in portion 441 for insertion of the blocking sheet 45. So, when the first and the second clamping sheets 31. 32 are abutted upon each other, a notch 323 of the carrier 3 will be formed naturally. And when the carrier 3 is installed in the receiving tank 4, a tight clinging effect will be formed among the bottom blocking piece 44, the blocking sheet 45 and the carrier 3 in favor of preventing leakage of the gel (G). In particular, an outwardly bent portion 313 can be provided on the top end of each first clamping sheet 31 for the convenience of injecting the gel (G) and the dismantling of the two clamping sheets afterwards. Moreover, a convex grasp portion 324 can be provided on the top end of one of the clamping sheets (the second clamping sheet 32 as in the drawing) of the carriers 3 as shown in FIG. 15. And a finger hole 325 is provided on the grasp portion 324 in order that the operator grasps a carrier 3 to pull out the carrier 3 from the receiving tank 4 smoothly or to place the carrier 3 in conveniently.

The electrophoresis separator of the present invention is provided with one slot on each side of the receiving tank to communicate with the electrophoresis tank. One side of each carrier is provided with a notch in corresponding to one of the slots, so that the gel can contact the electric conducting liquid in the electrophoresis tank through the slot. And the other ends of the gel will contact the electric conducting liquid in the receiving tank through the upper openings of the carriers directly. When the electrodes in the electrophoresis tank and the receiving tank are activated, the electrons produced in the receiving tank by the electrodes can be drifted to the electrodes of the electrophoresis tank through the gel on the carriers. Thus electric current floating is resulted to cause an effect of molecule separation and analysis of the sample in the gel, and a device of a practicable preferred structure of the electrophoresis separating engineering is provided accordingly.

Having thus described my invention, what I claim as new and desire to be secured by Letters Patent of the United States are:

1. A electrophoresis separator comprising an electrophoresis tank and a receiving tank as its main body; electrodes for driving electric current being provided separately in said electrophoresis tank and said receiving tank which are filled with electric conducting liquid to form an electric current passage; and said electrophoresis separator being characterized in that:

said receiving tank is used for placing carriers therein and provided with a slot on each side thereof to communication with said electrophoresis tank; one side of each of said carriers is provided with a notch corresponding to one of said slots in order that after a sample solution is dropped on said carriers, said carriers are directly inserted in said receiving tank; a bottom blocking piece provided at the bottom of said receiving tank directly covers the bottoms of said carriers and crevices between said notches and said receiving tank; blocking sheets are inserted into said slots and notches, said blocking sheets are removed from said slots and notches after a gel filled in said carriers is fixed and shaped, and thus said gel contacts said electric conducting liquid in said electrophoresis tank through said slots and notches; the other ends of the bodies of said gel in said carriers contacts said electric conducting liquid in said receiving tank through upper openings of said carriers directly, so that when said electrodes in said electrophoresis tank and said receiving tank are activated, electrons produced in said receiving tank by said electrodes drift to said electrodes of said electrophoresis tank through said gel in said carriers; and thus electric current floating causes an effect of molecule separation and analysis for samples in said gel, wherein said carriers are formed each by sure positioning of a first clamping sheet and a second clamping sheet to form a structure to receive said sample solution; positioning pins and positioning holes are provided on said two clamning sheets separately; and protruding sockets all of a specific height are provided on one of said clamping sheets at the surface to be contacted with the other of said clamping sheets, wherein when said two clamping sheets are abutted upon each other, said protruding sockets form a crevice between said two clamping sheets to enable an operator to position said two clamping sheets of said carrier promptly and get a thickness of said gel accurately after shaping, and wherein clamping members are provided on one of said first and second clamping sheets of each of said carriers, so that when said two clamping sheets are abutted upon and positioned relative to each other, said clamping members are directly used to fixedly clamp said two clamping sheets and assure firmness of said structure.

2. An electrophoresis separator as claimed in claim 1, wherein, an elastic sheet is sandwiched between said first and second clamping sheets of each of said carriers in order to increase compactness between said two clamping sheets and help shaping of said gel so as to avoid gel spilling.

3. An electrophoresis separator as claimed in claim 1, wherein, a convex grasp portion is provided on the top end of one of said first and second clamping sheets of each of said carriers in order that an operator grasps said carrier.

4. An electrophoresis separator as claimed in claim 1, wherein, a finger hole is provided on said grasp portion for insertion of fingers.

5. An electrophoresis separator as claimed in claim 1, wherein, said notches formed at the sides of said carriers are directly provided each at the bottom of a corresponding one of said first and second clamping sheets, and two fitting-in portions are provided respectively on said bottom blocking pieces to match and fit in said notches, an opening being provided at each of said fitting-in portions for insertion of said blocking sheets.

6. An electrophoresis separator as claimed in claim 1, wherein, positioning members are provided in said electrophoresis tank to fix said receiving tank therein.

7. An electrophoresis separator as claimed in claim 1, wherein, a cathode and an anode of said electrodes are provided simultaneously on the top of said receiving tank, said cathode and anode being connected to said electric conducting liquid in said electrophoresis tank and receiving tank via conductors; and an upper lid is used to cover said reaction separator device, an electrode connector being provided on said upper lid in favor of supplying electric current for said electrodes.

8. An electrophoresis separator as claimed in claim 1, wherein, positioning grooves are provided in said receiving tank to position said carriers, and press fixers are provided on the top of said receiving tank to fix said carriers.

* * * * *